United States Patent [19]

Marks

[11] Patent Number: 4,774,177
[45] Date of Patent: Sep. 27, 1988

[54] IMMUNOASSAY METHOD FOR DETECTION OF ANTIBODIES AND ANTIGENS

[75] Inventor: Janet M. Marks, Coronado, Calif.

[73] Assignee: Vet-Test Partners, San Diego, Calif.

[21] Appl. No.: 755,189

[22] Filed: Jul. 15, 1985

[51] Int. Cl.[4] .................... G01N 33/53; G01N 33/544
[52] U.S. Cl. .......................................... 435/7; 435/21; 435/28; 436/530; 436/810
[58] Field of Search .................... 436/530, 810; 435/7, 435/21, 28

[56] References Cited

U.S. PATENT DOCUMENTS 4,446,232 10/1981 Liotta ............................. 435/7
4,452,901 6/1984 Gordon et al. .................. 436/506

FOREIGN PATENT DOCUMENTS 0080108 1/1983 European Pat. Off. .

OTHER PUBLICATIONS

Hawkes et al., Analytical Biochemistry, vol. 119 (1982), pp. 142–147.
W. Neal Burnetti: "Western Blotting" etc.; 112 Analytical Biochemistry, 195–203 (1981), pp. 195–203.
Christiane Rordorf et al., "A Multidot Immunobinding Assay (etc.), 59 Journal of Immunological Methods 105–112 (1983).
McDougall et al., "Immunidot Assay . . . etc." 63 Journal of Immunological Methods 281–290 (1983).
Jan Marks, "Minimizing the Problems of Collecting Blood", Veterinary Medicine, Dec. 1984, pp. 1497–1500.

Primary Examiner—Sam Rosen
Attorney, Agent, or Firm—Owen, Wickersham & Erickson

[57] ABSTRACT

A method for detecting the presence of antibody or antigen in a liquid sample suspected of containing the antibody or antigen. To a test panel comprising a nitrocellulose carrier having stably bonded thereto a micro-sized spot consisting of either a primary ligand for that antibody or an antibody for that antigen, is added sufficient liquid containing non-specific globulin for the material of the spot, to block adjacent binding sites. Then a small liquid drop of the sample suspected of containing the antibody or antigen is added. After incubation of the panel, in tests for detecting an antibody, a drop of liquid containing labeled antiglobulin, which is an anti-immunoglobulin for that antibody, is added. In tests for detecting an antigen, the specific antibody-enzyme conjugate is added. After further incubation wash solution is added to the spot, and the test panel is assayed for presence of the label.

22 Claims, 1 Drawing Sheet

IMMUNOASSAY METHOD FOR DETECTION OF ANTIBODIES AND ANTIGENS

This invention relates to a method and apparatus for carrying out various immunoassays and in particular to immunoassays for determining the presence of an antibody in a sample suspected of containing the antibody or of an antigen in a sample suspected of containing that antigen. The apparatus comprises a novel test strip and a novel test kit.

BACKGROUND OF THE INVENTION

Enzyme immunoassays and radioimmunoassays have been developed to determine the existence and concentration of antibodies in body fluids or tissues from animals, humans, and plants. The enzyme-linked immunosorbent assay (ELISA) is one type of enzyme immunoassay used as a diagnostic tool for this purpose. Several different ELISA methods are available. The indirect method for antibody assay uses an antigen attached to a support. The antibody is reacted with an antigen specific for the antibody and allowed to bind to the antigen. The resulting antigen-antibody complex is incubated with an enzyme-labeled antiprimary species of immunoglobulin (i.e., cat-dog). An enzyme substrate is then added, and the amount of enzymatic activity is measured. The enzyme activity is related to the amount of antibody bound to the antigen.

These immunoassays are based on the premise that the clinician can obtain a sufficient amount of specimens of the fluids suspected of containing the antibody to enable performance of the test. Typically, the specimen size for such tests has been 150 microliters ($\mu$l) or more. In the case of small animals and newborn infants, this size poses a problem in obtaining a sample of body fluid in sufficient quantity to carry out the test.

An object of the present invention is to enable the performance of such a test with only about one $\mu$l of the body fluid.

Enzyme immunoassays have been desirable because the direct visualization of an antigen-antibody complex is thereby possible, using a chromogenic indicator. The interpretation of the test result has been dependent on a proper colorimetric determination. The color is not always easily observed with the unaided eye because of the background color in the environment of the specimen under test.

A dot-immunobinding assay for monoclonal and other antibodies has been proposed as a solution to these problems. The principle of that type of assay is as follows: A dilute solution or suspension of antigen is "dotted" on to a white, nitrocellulose piece of filter paper, and the dot is then incubated with test antibody and with a peroxidase-conjugated second antibody directed against the first antibody. After the development of the peroxidase, a positive reaction is detected as a colored dot against the white filter paper background. This assay has two advantages over other immunoassays. First, the amounts of the antigen and antibody needed for the assay are less than was needed before, because of the small spot size. Second, the nitrocellulose paper provides a background which is almost white, so that viewing is easier. See *Analytical Biochemistry*, 119, 142-147 (1982).

A major disadvantage of the dot-immunobinding assay is that it involves a large number of dilution, incubation, and washing steps that are required to carry out the test, and these steps consume considerable elapsed time. As many as twenty-one steps are required in such an assay, and each step is time-consuming and subject to error. A standard assay of this type takes four to twenty-four hours to perform.

The same problems occur when testing for a suspected antigen.

Accordingly, an improved immunoassay for determining the existence and concentration of an antibody or antigen in a sample is needed. The immunoassay should be operable with extremely small quantities of the fluid being tested; the antigen-antibody reaction should be measured by means of a tagged immunoglobulin, and when the determination is based on a colorimetric determination, the color should be easily observed in the test environment; the assay should require a relatively few number of dilution, incubation, and washing steps, and it should provide accurate results in a relatively short time period.

Achieving these desirable results is among the objects of this invention.

SUMMARY OF THE INVENTION

This invention aids in fulfilling these needs by providing an improved immunoassay for detecting the presence of an antibody or antigen in a sample. The method utilizes a test strip of white nitrocellulose carrier having stably bonded thereto a microsized spot of a primary ligand. The test strip is treated with a liquid containing non-specific globulin for the primary ligand in order to block antibody binding sites other than the antibody binding sites of the primary ligand. The strip is blotted or rinsed under the tap and shaken, in order to remove the excess liquid.

The liquid sample suspected of containing the antibody is applied to the spot on the test strip. This sample may be very small and provided on a small disc of filter paper. Then the test strip is incubated at ambient temperature for a time sufficient to bind the antibody that may be present in the sample to the primary ligand to form a ligand-antibody complex. This takes no more than about six minutes. The strip is blotted or rinsed under an ordinary tap and excess liquid shaken off.

A liquid containing labeled antiglobulin is then added to the complex. The antiglobulin is an anti-primary species of anti-immunoglobulin. The strip is blotted or rinsed and shook again to remove excess liquid. The test panel is then incubated at ambient temperature for a time, usually up to about 3 minutes, sufficient to bind the labeled antiglobulin to the antibody-ligand complex.

The strip is then ready to be assayed for presence of the label. The assay is preferably done by applying a suitable color developer to the strip.

This invention provides several advantages over immunoassays. First, this invention preserves the beneficial features of dot-immunobinding assays for monoclonal and other antibodies. Second, the amount of the antigen required is greatly reduced, typically to less than one $\mu$l. because of the extremely small spot size, about three mm in diameter. Third, the use of nitrocellulose paper permits the colorimetric reaction, if present, to be viewed against a background that should be almost white; hence the discriminatory power is greater than in another environment, such as a microtiter plate, and it becomes much easier to detect positive reactions and to reject false positives. Fourth, this invention provides the additional benefits of a considerable reduction in the time required to carry out the assay, reducing it from about 8–24 hours to about 10 to 15 minutes. Fifth, there is a drastic reduction in the number of dilution, incubation, and washing steps and a concomitant lessening of the risk for error.

The invention can be applied to humans, animals and plants.

DESCRIPTION OF SOME PREFERRED EMBODIMENTS

Figure 1:
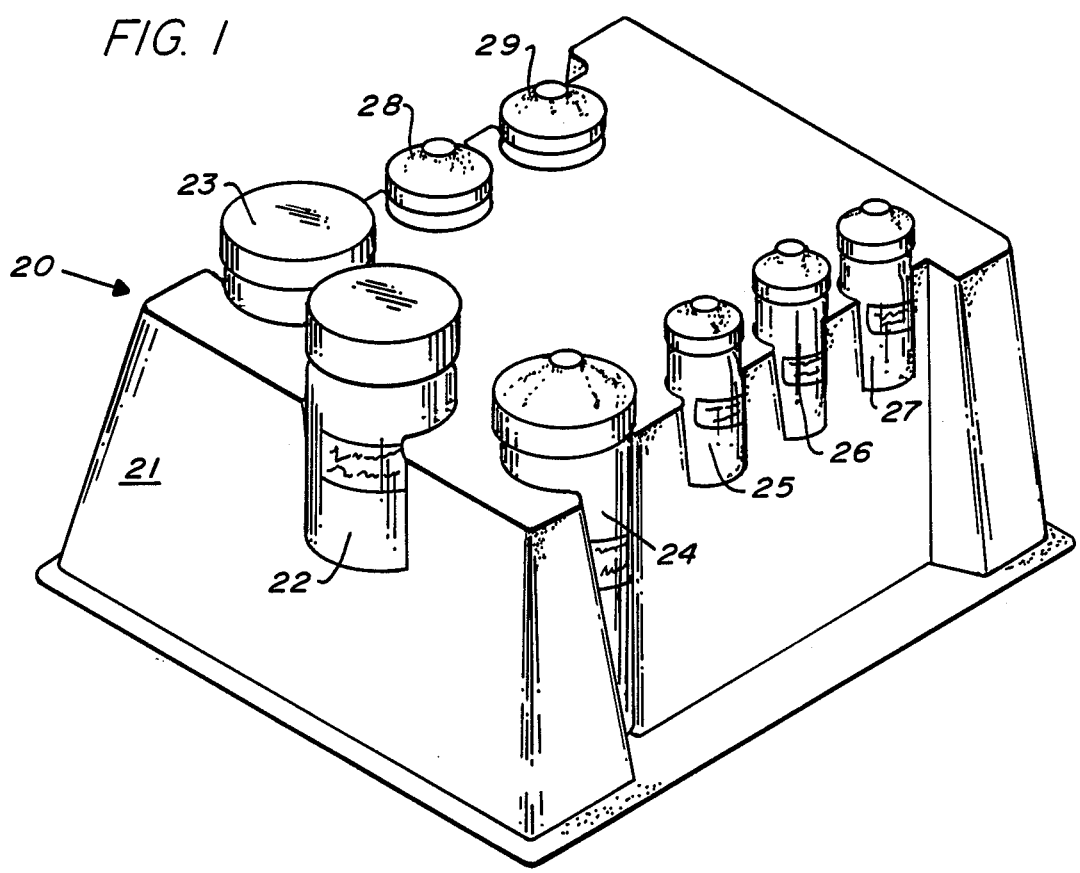
FIG. 1 is a view in perspective of a kit embodying the principles of the invention.

This invention can be employed to detect the presence of an antibody or immunoglobulin (Ig) in a sample suspected of containing the immunoglobulin or antibody. The terms "immunoglobulin" and "antibody" are used inter-changeably herein, and these terms include within their meanings immunoglobulin fragments containing a combining site, such as Fab fragments or F(ab)$_2$ fragments. Ordinarily, the immunoglobulin is derived from fluid taken from a human or animal subject. The immunoglobulin can be of any class or subclass. For example, the invention can be employed to assay IgG, IgM, IgA, IgD or IgE in a fluid sample. The immunoglobulin can also be derived from other sources. For example, this invention can be employed to assay monoclonal antibodies produced by hybridomas.

The invention can also be used to detect the presence of an antigen in a sample suspected of containing that antigen. For this purpose the nitrocellulose support is earlier pre-impregnated and immobilized with the antibody specific for the antigen to be measured. The patient sample (antigen) and specific antibody-enzyme conjugate is added to the nitrocellulose support. When the specific antigen is present in the sample, the antigen, having multiple binding sites, is bound immunologically to both the pre-impregnated antibody and the enzyme conjugated antibody. After addition of the substrate, a distinctly colored reaction product is formed only if the nitrocellulose support contains immunological immobilized enzymes.

The ligand employed in this invention to detect the immunoglobulin is any organic substance that can interact with the combining site of the immunoglobulin and bind to the immunoglobulin. The ligand is an antigen or hapten. The ligand can be monoepitopic or polyepitopic. In the case of a hapten, the hapten canbe bound to a carrier, if necessary, and then employed in the invention. This invention is not restricted to any specific ligand or to a ligand of any particular molecular weight or size.

The ligand is typically derived from a polypeptide, polysaccharide, lipid or nucleic acid, or groups of subunits or mixtures of these substances. The ligand can also be derived from assemblages, such as bacteria, fungi, various organelles, such as mitrochondria or nuclei, cell membranes, or fragments of these and like materials. The ligand can be an antigen in the form of a protozoa, such as microfilaria for heartworm (*Dirofilaria immitis*), or virus, such as coronavirus, parvovirus or distemper. Other organic substances, such as drugs, can also function as ligands.

The ligand should be in substantially pure form to avoid antibody cross-reactions and false positive or false negative results. Nevertheless, it is difficult in practice to eliminate foreign antigens and haptenic materials from the test site, and for this reason the expression "primary ligand" is used herein to refer to the ligand that is known to be specific for the binding site of the antibody whose presence is to be determined. A general procedure for preparing antigens is described below, under the heading "Procedure for preparing the ligand".

An anti-immunoglobulin to the antibody is utilized in the assay of this invention. In general, the anti-immunoglobulin is an anti-primary species immunoglobulin, such as antiserum. For example, in the case of an immuno-assay for heartworm in the dog, a suitable anti-immunoglobulin has been found to be goat anti-dog IgG. For a similar assay involving cats, goat anti-cat IgG is suitable. While some anti-immunoglobulins are commercially available, others can be prepared using conventional immunological techniques.

The ligand-antibody reaction can be made visible by attaching a tag to the anti-immunoglobulin as long as the tag is a molecule demonstrable through some special property. For example, an anti-immunoglobulin having a fluorescent tag can be detected by ultra-violet light. Presently, a fluorescent label is used predominantly with microfilaria immitis antigen. Immunoferritic tags utilize high electron-scanning capacity and radioimmunoassay tags utilize radioactivity. An enzyme labeled anti-immunoglobulin to the antibody can also be employed to produce color if the antibody is present, and the color can be visible in ordinary light. All of these tags provide powerful techniques for assaying antibodies according to this invention and for identifying characteristic disease-related antibodies in clinical diagnoses. Tagged anti-immunoglobulins are commercially available or can be readily prepared using conventional polyclonal and monoclonal techniques.

Enzymes that catalyze the formation of visible product can be coupled to the anti-immunoglobulin using bifunctional cross-linking reagents without destroying the activity of the enzyme or the antibody. For example, horseradish peroxidase is a preferred enzyme because it is readily available and relatively inexpensive. The enzyme can be coupled to a specific anti-immunoglobulin, which in turn is bound to the antibody whose presence is to be determined. This enzyme will convert added hydrogen peroxide to oxygen free radicals. The radicals can in turn react with a chromogenic precursor, such as 3', 3'-diaminobenzidene or 4-chloro-1-naphthol, added with the peroxide to form an insoluble colored precipitate.

A suitable color developer for horseradish peroxidase comprises:

1 ml. 100% methanol (containing 4-chloro-1-naphthol, 3 mg./ml.)

3 ml. tris buffered saline (50 mM tris-HCl, 200 mM NaCl, pH −7.4)

1 drop 3% $H_2O_2$ (hydrogen peroxide, aqueous solution).

A suitable carrier is nitrocellulose paper or a nitrocellulose precursor that is converted to the required composition prior to use. The nitrocellulose carrier can be of any size or shape. It can be a laminate, self-supporting or supported from below, rigid or flexible, opaque, translucent or transparent. The carrier can be smooth or uneven, or can be a woven, cast or extruded material. The carrier can be in the form of a panel, preferably an elongated strip. Nitrocellulose paper is hydrophobic by nature and should be made wettable by known techniques when employed with aqueous solutions. Nitrocellulose paper can be sterilized, such as by treatment with ethylene oxide, or autoclaved at 121° C. at 15 psi for about 30 minutes.

The nitrocellulose carrier immobilizes the primary ligand through a variety of mechanisms. Binding properties of nitrocellulose are a combination of interactions which include hydrophobic interactions, electrostatic interactions, salt bridges and hydrogen bonding. A nitrocellulose paper having a small pore size provides an increased surface area and corresponding higher binding capacity for the ligand.

Nitrocellulose paper is versatile and immobilizes many of the ligands previously described. It can be employed in capillary and electroferretic transfers, plaque lifts and filter-hybridization. Nitrocellulose paper is well suited for use in all applications where protein dyes are employed and for transfer of basic proteins. It can also be employed in trichloroacetic acid precipitations and dissolved for scintillation counting.

PROCEDURE FOR PREPARING THE LIGAND

A general procedure for preparing ligands for use in the invention is illustrated by procedure used for preparation of antigen from *Dirofilaria immitis* in an assay for heartworm. Other antigens can be prepared similarly, usually with modifications.

Adult *Dirofilaria immitis* were aseptically removed from the hearts of infected dogs, washed several times in sterile phosphate buffered saline (PBS) having a pH of 7.4 and transferred to sterile tissue culture flasks (Corning) containing 300 ml. of RPMI-1640 media (pH=7.4) with 1 $\mu$g of gentamycin. The adults were cultured for several weeks at 37° C. with daily medium changes. The adult worms, which still contained microfilariae, were then taken from the culture flasks, frozen at $-80°$ C. and lyophilized.

The lyophilized material was suspended at 30 mg/ml in cold phosphate buffered saline having a pH of 7.4 and homogenized using a Polytron ultrasonicator. The adult microfilaria homogenate was diluted to 10 mg/ml by the addition of PBS and extracted for 12 hours at 4° C. with constant stirring. The insoluble material was pelleted by centrifugation at 700x G for 20 minutes. The supernatant was saved and the pellet resuspended with the same volume of PBS and then extracted for an additional 18 hours at 4° C. with constant stirring. The insoluble material was removed by centrifugation (700x G for 20 minutes) and the extraction supernatants were pooled. The remaining suspended matter was removed by centrifugation at 40,000x G for 1 hour at 4° C.

A 10% (w/v) solution of trichloroacetic acid (TCA) was added in a dropwise manner to a final concentration of 20 mM. TCA precipitation proceeded for 30 minutes at 2320 C. with constant stirring. The TCA precipitable material was pelleted by centrifugation at 10,000x G for 30 minutes at 4° C. The material in the supernate was designated the TCA soluble (TCAS) antigen. TCAS antigen was dialyzed extensively against 0.5M ammonuim bicarbonate (pH=7.2) until the TCAS solution approached a neutral pH. The TCAS antigen was concentrated by lyophilization and stored at $-20°$ C. until used.

Lectin affinity materials were obtained from Vector Laboratories. Peanut agglutinin (PNA) was bound to agarose at 5 mg. of PNA/ml of settled gel.

A 20 cm×0.5 cm glass column was filled with 5 ml of gel. Columns were equilibrated with 0.9% NaCl containing 0.04% $NaN_3$. A TCA-soluble fraction was applied to the column. The column was washed until the absorbance at 280 mM fell to zero. Bound glycoprotein was eluted with 500 mM galactose, 500 mM NaCl, 0.04% $NaN_3$ for PNA column. Fractions were pooled and concentrated by ultrafiltration. The PNA-antigen preparation was stored at $-20°$ C. until needed.

Other antigens can be prepared in the above manner with some modifications depending upon the anti-immunoglobulin (IgG). In some cases, the antigen required for a particular immunoassay will be commercially available. The described method is especially advantageous because the special purification steps yield a product of high quality thereby reducing the likelihood of antibody cross-reactions.

PROCEDURE FOR PREPARING THE NITROCELLULOSE CARRIER

Figure 2:
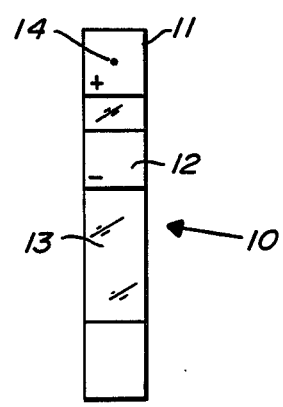
FIG. 2 is a plan view of a test strip of the invention.

A test strip or nitrocellulose carrier 10 (See FIG. 2) for use in this invention can be prepared as follows. A sheet of nitrocellulose paper is conveniently divided by pencil lines into a rectangular grid. The nitrocellulose paper is washed by soaking it in deionized water to activate the paper. A wash-time of about ten minutes at room temperature is typically sufficient to activate the paper, so that the ligand will be bound to the sheet or strip by physical entrapment, covalent bonding, ionic bonding, absorption, adsorption or combinations of these interactions.

The nitrocellulose paper is removed from the deionized water, drained and then dried to form a substantially dry, activated carrier for the ligand. The paper would be dried under conditions that will not adversely affect the stability of the nitrocellulose or deactivate the strip. Since the nitrocellulose paper may be adversely affected by heat, air drying at room temperature is preferred. Substantially sterile conditions are preferred throughout.

Two squares 11 and 12 (See FIG. 2) of the dried paper or carrier may then be applied to a strip 13 of suitable material such as a clear plastic like that used for photographic film. Preferably, the squares 11 and 12 are apart.

The ligand is then spotted on the nitrocellulose paper as follows. When the nitrocellulose paper is dry, a spot 14 as small as possible of the primary ligand is placed on the carrier square 11. The ligand can be applied to the carrier 11 in solution or suspension in a liquid. The concentration of the ligand in the liquid will vary from ligand to ligand and with the particular disease state being measured. The concentration of ligand should provide a sufficient number of determinants to bind antibody in an amount effective to form an observable spot when the tagged antiglobulin is assayed. If the liquid containing the ligand is very dilute, it is possible to apply successive doses at the same site, taking care only that the strip portion 11 is allowed to dry between each such application. For *Dirofilaria immitis* antigen, as little as 0.2 mg/ml can be spotted in each square of the grid on the paper before the squares 11 are cut out. The volume of the liquid is of extremely small size, e.g., about one $\mu$l, but should be in an amount sufficient to form an observable spot. Typically, a microsized spot 14 having a maximum dimension of about 3 mm will be formed on the nitrocellulose paper strip portion 11. Virus and bacteria can be applied directly to the nitrocellulose paper.

The strip portion 11 is dried at about 60° C. to about 80° C. to stabilize the binding of the primary ligand to the nitrocellulose paper. Drying can typically be carried out in a temperature controlled oven for about 45 minutes in the case of nitrocellulose paper. The resulting antigen-spotted test panel 10 can then be stored for several months without any loss of activity. The strip should be stored at a cool temperature, such as in a refrigerator, and out of direct sunlight. For optimum results, the test panel 10 should be used within about one year.

While the preparation of the test strip 10 has been described for a single ligand in one location on the strip, it will be understood that the ligand can be spotted at multiple locations on the strip 10 and that ligands of different types can be spotted at different locations on the strip so that different antibodies can be assayed on the same paper strip or a single antibody can be assayed for receptivity to different antigens. Similarly, a suitable antibody can be applied for a test for an antigen.

It will also be understood that a bridging material can be interposed between the primary ligand and the nitrocellulose paper. While this invention can be employed to assay any biological fluid, such as whole blood, serum, plasma, urine, saliva or other fluid or secretion, a binding material may limit the range of fluids that can be assayed.

PROCEDURE FOR CARRYING OUT THE IMMUNOASSAY

While the test strip 10 contains the primary ligand, which is the ligand specific for the antibody of interest, other antigens and haptens may be bound to the nitrocellulose paper, for example on the square 12. Because of the possibility of antibody-antigen cross-reactions, it is desirable to block the antigens and haptens other than the primary ligand. Blocking can be carried out by soaking each nitrocellulose test strip portion 11 or 12 with a washing solution containing a blocking agent for a sufficient time for antibody and antigen or hapten that may be present to interact. This incubation time will typically be about 30 seconds. A typical washing solution contains 3% w/v bovine serum albumen and 1% v/v antiprimary species globulin. In some assays the bovine serum albumen can be omitted. The test strip 10 is blotted or rinsed with tap water and shaken off to remove excess washing solution. For blotting, a soft, spongy material or clean, absorbent paper is suitable for this purpose, or it can be rinsed with water from an ordinary tap. The non-specific antigens and haptens are now suitably blocked on the test strip.

The test strip 10 is now ready to receive the sample suspected of containing the antibody. The sample suspected of containing the antibody is prepared for use by dilution in the wash solution. For example, a blood sample can be undiluted or diluted 1:100-1:1000 etc. with the wash solution. A drop of the diluted patient sample is applied to the test strip portion 11 and incubated to allow the primary ligand and antibody that may be present to interact to form antibody-ligand complex. Incubation at ambient temperature for a time period of at least about six minutes is sufficient. The test strip 10 is blotted to remove excess amount of the liquid sample, or rinsed under the tap and excess liquid shaken off.

In the conventional dot-immunobinding assay this incubation step requires 2 to 4 hours, and in some cases incubation overnight. The incubation time is greatly reduced in the assay of this invention, usually lasting no more than six or seven minutes. In addition, the conventional assay requires subsequent washing of a panel or strip for 30 minutes in several changes of tris-buffered saline followed by a repeat of the blocking step. The assay of this invention eliminates these time-consuming steps and the possibility for error arising during these steps.

A drop of the tagged anti-immunoglobulin is added to the test strip 10. Dilutions should be made in the wash solution. Once again the test strip 10 is incubated at ambient temperature for a time sufficient to bind the tagged anti-immunoglobulin to the antibody-ligand complex that may be present on the test strip 10. Incubation at room temperature for a time of at least 3 minutes is typical. This time is substantially shorter than the time required in the conventional dot-immunobinding assay. The test strip 10 is freed from excess liquid, as by blotting or washing. Washing may comprise rinsing with water (tap water may be used for for rinsing at any stage of this invention) and then excess shaken off.

This invention dispenses with the need to wash the strip 10 several times in tris-buffered saline, as is required in the conventional assay.

The test strip 10 is then assayed to determine the existence, and, if desired, the concentration, of the tag on the microsized spot 14. In the case of an enzyme tag, this can be conveniently carried out by adding substrate for the enzyme to the spot 14 and determining enzymatic activity. There will be no enzymatic activity if the antibody or antigen was absent from the sample tested. On the other hand, the extent of enzymatic activity will be a measure of the existence and concentration of the antibody or antigen in the sample.

In the assay for antibody to *Dirofilaria immitis* in the dog or cat, a fluid specimen from the animal was added to a prepared test strip 10 as previously described. A drop of peroxidase conjugated goat anti-dog (or anticat) IgG (1:50-1:100 dilution) was added to the nitrocellulose test strip 10. The test strip 10 was incubated at room temperature for 3 minutes. The test strip 10 was blotted with clean, absorbent paper (it could have been rinsed under a tap and shaken off). One drop of color developer was added to the test strip 10, incubated for 1 minute, and read. Using the color developer previously described, a positive result for the antibody or antigen indicated by a blue color in about 10 seconds to 90 seconds. No color change is an indication of the absence of antibody or antigen in the sample tested. Positive and negative control strip are also provided and run exactly like the patient's strip.

The immunoassay of this invention can be carried out at ambient temperature. The assay can be performed at a pH of about 7 to about 8, slightly alkaline pH being preferred. The entire procedure for carrying out the immunoassay of the invention can be completed in about 10 minutes or less.

The test procedure can be summarized as follows:

Dilute the blood sample 1:100-1:1000 with wash (blocking) solution.
1. Add 1 drop of wash solution to the test strip 10.
2. Blot (with any clean absorbent paper), or rinse with tap water and shake off excess liquid, whatever the operator prefers.
3. Add 1 drop of diluted patient sample 14 to the test strip 10: and incubate the strip at room temperature for 6 minutes.
4. Blot, or rinse under tap and shake off excess liquid.

5. Add 1 drop of Peroxidase conjugated goat anti-dog IgG (1:50–1:100 dilution) to the spot 14 and incubate at room temperature for 3 minutes.
6. Blot, or rinse under tap and shake off excess liquid.
7. Add 1 drop of color developer to the spot 14, and incubate for 1 minute.
8. Blot (or rinse under tap and shake) and read. POSITIVE Primary Antibodies give a blue color in about 30 seconds to about ninety seconds. NEGATIVE Primary Antibodies will show no color.

A POSITIVE and NEGATIVE control strip is provided, and it is run exactly like the patient's strip 10, except for steps 3 and 4.

EXAMPLE 1

PROCEDURE FOR CANINE HEARTWORM TEST
1. Wet a control strip and a patient test strip with blocking solution. Rinse the patient test strip only under tap, and shake off excess water (or blot, if preferred).
2. Add 1 drop of the 1:500 patient sample to the patient strip. Wait 6 minutes.
3. Rinse both the control strip and the patient test strip under tap; shake off excess water. (Or blot if preferred.)
4. Add 1 drop of Anti-dog IgG HRP (horseradish peroxidase) to each of the control strip and the patient strip. Wait 3 minutes. Rinse under tap, and shake off excess water. (Or blot if preferred.)
5. Add one drop of coloring solution to each strip 1 ml. 4-chloro-1-napthol in 100% methanol 3 mg/ml TBS—i.e., tris buffered saline (50 mM tris-HCl, 200 mM NaCl, pH 7.4) 1 drop of 3% hydrogen peroxide aqueous solution. Wait 1 minute. Rinse under tap and shake off excess water. (Or blot if preferred.)
6. Read result.

In summary, this invention is useful for detecting antibodies or antigens in extremely small amounts in any type of fluid samples. It is particularly useful for assaying monoclonal antibodies and for immunodiagnosis for pathological antibodies in human and animal body fluids and in plant tissues. This invention provides an immunoassay having universal application in immunodiagnosis; it is not limited to assaying antibodies from a specific source or of a particular type. Because the nitrocellulose paper is white in color, the discriminatory power for observing a color change is greatly enhanced. When compared with the known dot-immunobinding assay, the assay of this invention is much simpler and less time-consuming to carry out. The assay of this invention makes it possible to reduce the number of dilution, incubation and washing steps and thereby reduce the risk of error.

EXAMPLE 2

ALFALFA MOSAIC VIRUS

A nitrocellulose carrier is impregnated and immobilized with goat polycolonal alfalfa mosaic antibody, which is grown in a goat. The plant sample is macerated in phosphate buffered saline, and one drop of this sample is added to the nitrocellulose carrier and incubated for 6 minutes at ambient temperature, then blotted or rinsed with water.

Next mouse monocolonal (AMV) antibody is added to the nitrocellulose carrier and rabbit anti-mouse IgG conjugated with either horseradish peroxidase or alkaline phosphatase is also added to the carrier. After incubation for 3 minutes at ambient temperature, color developer is added and read. The alkaline phosphatase choromogenic indicator may be nitrobluetetrazolium (NBT) and 5-bromo-4 chloro-3 indolyl phosphate (BCIP). The color developer may thus comprise:

(NBI component)
15 mg. nitrobluetetrazolium
5 ml hot 0.01M tris-HCl-0.1M NaCl (pH 9.8)–0.005M magnesium chloride (BCIP component)
7.5 mg 5-bromo-4 chloro-3 indolyl phosphate
50 ml. DMSO (dimethylsulfoxide) in 1 ml. 2M tris-HCl pH 9.8.

The BCIP and NBT components are combined and diluted to 50 ml.

Test kits

Test kits embodying the invention make the invention easy to use outside a special laboratory by the veterinarian or doctor. As shown in FIG. 1, a test kit 20 may comprise a holder or container 21 with a series of compartments that hold vials. The reagents that are used may be as follows:

Wash (blocking) solution:
3% w/v bovine serum albumin/1% v/v normal goat serum. Alternatively, the goat serum can be replaced with 10% horse serum or fetal calf serum. In some assays Bovine serum albumin can be omitted.

Horseradish Peroxidase-Conjugated
(Anti-primary species immunoglobulin).

For Example:
When the test antibody was raised in goats, use peroxidase-linked goat-anti dog IgG, or peroxidase-linked goat-anti cat IgG.

Color Developer:
1 ml. 100% methanol containing dissolved 4-chloro-1-naphthol, 3 mg/ml
3 ml. tris buffer saline (50 mM tris-HCl, 200 mM NaCl, pH, 7.4), and
1 drop 3% $H_2O_2$ (hydrogen peroxide) aqueous solution.

Each kit may be directed to one type of test. For example, a canine parvovirus test kit is made as follows:
1. A main container 21 for the entire kit 20.
2. A vial 22 containing a plurality of nitrocellulose test strips—impregnated and immobilized with the specific antigen.
3. A vial 23 containing a series of nitrocellulose control strips—canine origin positive and negative.
4. A squeeze bottle 24 contaning washing or blocking solution (e.g., 3% w/v bovine serum albumin and 1% v/v normal rabbit serum.
5. A vial 25 containing horseradish-peroxidase-conjugated rabbit (or goat) anti-canine IgG 1:50–1:100 dilution.
6. A vial 26 containing - 4-chloro-1-naphthol in methanol.
7. A vial 27 containing - tris-buffered saline. Aqueous solution.
8. A vial 28 containing - hydrogen peroxide 3% aqueous solution.
9. An empty vial 29 with 1 ml. and 5 ml. graduations for preparation of color developer.

This test kit 20 can also be used for testing canine distemper or for canine brucellosis by using a test strip impregnated and immobilized with the appropriate specific antigen. For canine brucellosis the dilution in the vial 25 can be from 1:25 to 1:100 dilution.

For a test kit for feline infectious peritonitis or coronavirus the differences are the use of paper impregnated and immobilized with the specific antigen, the use of a control strip that is feline positive and negative, and the substitution at #5 of a vial 25 containing horseradish peroxidase conjugated rabbit (or goat) anti-feline IgG at 1:50 to 1:100 dilution.

For a test kit 20 for bovine brucellosis, the only changes needed are, first at #5 where the vial 25 contains horseradish—peroxidase—conjugated rabbit (or goat) anti-bovine IgG at 1:25 to 1:100 dilution. Also, the test and control strips respectively contain the specific soluble antigen and the use of bovine origin positive and negative on the control strip.

For heartworm (for detection of *Dirofilaria immitis* in dog or cat) the kit contains test strips impregnated and immobilized with the specific antigen and control strips with either canine or feline positive and negative, as appropriate. Similarly, the vial 25 will contain either horseradish-peroxidase-conjugate goat anti canine or anti feline IgG, 1:50 to 1:100 dilution.

For *Salmonella dublin*, the test kit contains nitrocellulose test strips impregnated and immobilized with the specific antigen, and nitrocellulose control strips with bovine origin positive and negative. The vial 25 contains horseradish-peroxidase-conjugate rabbit or goat anti-bovine IgG at 1:25 to 1:100 dilution.

For *Toxoplasmosis gondii*, the test kits's strips are impregnated and immobilized with the specific antigen, the controls strips have feline (or human) origin positive and negative, and the vial 25 may have horseradish-peroxidase-conjugate rabbit or goat anti-feline (or anti human) IgG at 1:50 dilution.

For avian influenza virus tests, the kit's test strips are impregnated and immobilized with the specific antigen, and the control strips have avian origin positive and negative. Also, the vial 25 contains horseradish-peroxidase-conjugate of rabbit or goat or chicken anti-avian IgG at 1:25 dilution. In the squeeze bottle 24, the washing solution may use normal goat, rabbit, or chicken serum.

For avian Newcastle's virus, the specific antigen is used on test strip, with other ingredients the same as in the avian influenza test kit.

AMV

For alfalfa mosaic virus, the nitrocellulose carrier is impregnated and immobilized with goat poly-colonal alfalfa mosaic antibody which is grown in a goat. The kit includes phosphate buffered saline for macerating the plant sample, and a dropper. There is a vial of mouse monocolonal (AMV) antibody and one of rabbit anti-mouse IgG conjugated with either horseradish peroxidase or alkaline phosphatase. The color developer may be as for animals or may be the nitrobluetetrazolium (NBT) and 5-bromo-4 chloro-3 indolyl phoshate (BCIP) solution described above.

In general, each test will involve a test strip 10 impregnated and immobilized with the specific antigen for the sought antibody, the control strip with the type of animal tested, both positive and negative. The test kit will also include the color developer made from materials in the kit.

An example of a test kit for testing for a specific antigen is as follows:

Feline leukemia virus test kit 20 (FeIV)
1. A main container 21 for entire kit.
2. A vial 22 containing nitrocellulose test strip—impregnated and immobilized with specific antibody.
3. A vial 23 containing nitrocellulose control strip—feline origin positive and negative.
4. A squeeze bottle 24 of washing or blocking solution (3% w/v bovine serum albumin and 1% v/v normal rabbit serum.
5. A vial 25 containing horseradish-peroxidase-conjugate-specific antibody.
6. A vial 25 containing 4-chloro-1-naphthol in methanol.
7. A vial 27 containing tris-buffered saline aqueous solution.
8. A vial 28 containing hydrogen peroxide 3% aqueous solution.
9. An empty vial 29, with 1 ml. and 5 ml. graduations for preparation of color developer.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A method for detecting the presence of antibody or antigen in a liquid sample suspected of containing the antibody or antigen from a known biospecies comprising the steps of:
   (A) providing a test panel comprising a nitrocellulose carrier having stably bonded thereto a microsized spot consisting of either a primary ligand for said antibody or an antibody for said antigen,
   (B) adding to the sput on the test panel sufficient liquid containing globulin which is not specific to the biospecies being tested to block adjacent binding sites,
   (C) applying to said test panel a small liquid drop of the sample suspected of containing the antibody or antigen,
   (D) incubating the test panel and spot at ambient temperature for about six minutes, a time sufficient to bind the antibody or antigen suspected of being present in said sample to the material of said spot to form a ligand antibody complex,
   (E) adding to said complex a drop of liquid containing labeled antiglobulin, said antiglobulin being an anti-immunoglobulin for said antibody or antigen being tested for,
   (F) incubating said test panel and spot at ambient temperature for about 3 minutes, a time sufficient to bind said antiglobulin to said complex,
   (G) adding wash solution to said spot, and
   (H) assaying said test panel for presence of the label.

2. The method of claim 1 wherein said label is an enzyme.

3. The method of claim 2 wherein activity of said enzyme is assayed by
   adding to said spot a color developer comprising a substrate for said enzyme and a chromogenic indicator,
   incubating the test panel, and inspecting said spot for color change.

4. The method of claim 1 wherein said nitrocellulose test panel is pretreated by:
   (1) washing unactivated nitrocellulose carrier in deionized water to activate it,
   (2) drying the nitrocellulose carrier, (3) depositing on said activated carrier a fluid specimen containing said primary ligand or antibody, and (4) drying the carrier for a time sufficient to form said stable bond.

5. The method of claim 1 wherein said microsized spot is in the order of 3.0 mm. in diameter.

6. The method of claim 1 wherein each liquid is added in slight excess followed by blotting the test panel or washing it and shaking it to remove the excess liquid.

7. The method of claim 1 wherein the incubation time in step (D) is at least six minutes and the incubation time is step (F) is at least three minutes.

8. The method of claim 1 wherein the wash solution added in step (G) is the same solution as is added in step (B) for blocking.

9. A method for detecting the presence of antibody in a liquid sample taken from a known biospecies and suspected of containing the antibody, comprising the said method steps of:

(A) stably bonding a microsized spot of a primary ligand for said antibody to a strip of nitrocellulose paper, (B) adding to the paper strip a blocking-wash solution containing globulin, which is not specific to said biospecies, for said primary ligand, to block antibody binding sites other than antibody binding sites on said primary ligand, (C) applying to said spot the liquid sample suspected of containing the antibody, (D) incubating the spot at ambient temperature for about six minutes, a time sufficient to bind the antibody, if present, to said primary ligand to form a ligand-antibody-complex, (E) adding to said complex a liquid containing a labeled antiglobulin, which is an anti-immunoglobulin for said antibody, (F) incubating said complex at ambient temperature for about three minutes, a time sufficient to bind said antiglobulin to said antibody-ligand complex, and (G) assaying the resulting test panel for presence of labrl on said labeled antiglobulin.

10. The method of claim 9 wherein said label is horseradish peroxidase or alkaline phosphatase and its enzyme activity is assayed by adding to said spot a color developer comprising a substrate for that enzyme and a chromogenic indicator, incubating the spot panel, and inspecting said spot for color change.

11. The method of claim 10 wherein said primary ligand is *Dirofilaria immitis* adult antigen from a dog.

12. The method of claim 11 wherein said blocking wash solution comprises bovine serum albumin and normal goat serum, horse serum or fetal calf serum.

13. The method of claim 12 wherein said anti-immunoglobulin is goat anti-dog IgG.

14. The method of claim 10 wherein said horseradish peroxidase is conjugated to said anti-immunoglobulin.

15. The method according to claim 9 wherein said liquid sample is human, animal or plant tissue or human or animal serum, whole blood, plasma, or urine undiluted or diluted at least 1:100–1:1000 with said blocking-wash solution.

16. The method of claim 9 wherein said microsized spot is in the order of 3 mm. in diameter.

17. The method of claim 9 wherein each liquid is added in slight excess and then the paper is blotted to remove the excess.

18. The method of claim 9 wherein each liquid is added in slight excess, and then the paper is rinsed with water and shaken off.

19. The method of claim 9 wherein the incubation time is step (D) is at least six minutes and the incubation time in step (F) is at least three minutes.

20. The method of claim 9 wherein a wash solution is added between steps (F) and (G), said wash solution being the same solution as is added in step (B) for blocking.

21. The method for detecting the presence of antigen in a liquid sample suspected of containing the antigen, comprising the steps of:

(A) stably bonding a microsized spot of an antibody for said antigen to a nitrocellulose carrier, (B) adding to the carrier a blocking-wash solution containing non-specific globulin for the antigen primary ligand to block antigen binding sites other than on said antibody, (C) applying to said spot the liquid sample suspected of containing the antigen and specific antibody enzyme conjugate, (D) incubating the spot at ambient temperature for a time sufficient to bind the antigen which may be present in said sample, to the antibody to form antigen-antibody complex and an antigen-enzyme conjugate antibody complex, (E) adding blocking solution to said spot and removing excess liquid, and (F) assaying said spot for presence of enzyme label.

22. The method of claim 21 as applied to plants wherein said sample is plant material macerated in phosphate buffered saline.

* * * * *

UNITED STATES PATENT AND TRADEMARK OFFICE
CERTIFICATE OF CORRECTION

PATENT NO. : 4,774,177
DATED : September 27, 1988
INVENTOR(S) : Janet M. Marks

It is certified that error appears in the above-identified patent and that said Letters Patent are hereby corrected as shown below:

Column 5, line 54, "2320 C" should read --23° C--.

Column 12, line 8, "vial 25" should read --vial 26--.

Column 12, line 32, "sput" should read --spot--.

Column 13, line 13, "is step" should read --in step--.

Column 13, line 43, "labrl" should read --label--.

Signed and Sealed this

Fourteenth Day of March, 1989

Attest:

DONALD J. QUIGG

*Attesting Officer*  *Commissioner of Patents and Trademarks*